United States Patent

Hengeveld et al.

[11] Patent Number: 6,080,874
[45] Date of Patent: Jun. 27, 2000

[54] SYNTHESIS AND ISOLATION OF N-(ARYL OR HETEROARYL)-ALKYL-N-HYDROXYUREA

[75] Inventors: John E. Hengeveld, Kenosha, Wis.; Elise H. Leese, Libertyville, Ill.; Brian S. Moon, Holland, Mich.; Dennis M. Abad, Wheeling, Ill.; Kimberly A. Allen, Silver Lake, Wis.; Philip E. Bauer, Grayslake; David B. Murphey, Gurnee, both of Ill.; Brian T. Fohey, Kenosha; Richard R. Copp, Jr., Kenosha, both of Wis.; Greg S. Lannoye, Wildwood; Rodney M. Mittag, Chicago, both of Ill.

[73] Assignee: Abbott Laboratories, Abbott Park, Ill.

[21] Appl. No.: 09/161,126

[22] Filed: Sep. 25, 1998

Related U.S. Application Data

[60] Provisional application No. 60/059,663, Sep. 25, 1997.
[51] Int. Cl.[7] .................... C07D 333/56; C07D 307/78; C07D 307/02; C07D 273/00
[52] U.S. Cl. ................. 549/58; 549/75; 549/467; 549/469; 549/493; 564/56; 564/60; 564/61
[58] Field of Search ................ 549/58, 75, 467, 549/469, 493; 564/56, 60, 61

[56] References Cited

U.S. PATENT DOCUMENTS

| | | | |
|---|---|---|---|
| 4,873,259 | 10/1989 | Summers, Jr. et al. | 514/443 |
| 4,992,464 | 2/1991 | Brooks et al. | 514/443 |
| 5,026,729 | 6/1991 | Brooks et al. | 514/575 |
| 5,175,183 | 12/1992 | Brooks et al. | 514/438 |
| 5,185,363 | 2/1993 | Brooks et al. | 514/438 |
| 5,250,565 | 10/1993 | Brooks et al. | 514/443 |
| 5,288,896 | 2/1994 | Capiris et al. | 560/27 |
| 5,292,900 | 3/1994 | Bahsa et al. | 549/419 |
| 5,663,368 | 9/1997 | Flisak et al. | 549/57 |

FOREIGN PATENT DOCUMENTS

0459748 12/1991 European Pat. Off. .
9325544 12/1993 WIPO .

OTHER PUBLICATIONS

A.O. Stewart, et al., *J. Org. Chem.*, 1992, 57, 5020–5023.

*Primary Examiner*—Joseph K. McKane
*Assistant Examiner*—Joseph Murray
*Attorney, Agent, or Firm*—Lawrence S. Pope

[57] ABSTRACT

The present invention provides a simple, 1-step process for preparing a N-(aryl or heteroaryl)-hydroxyurea comprising reacting the corresponding alcohol, ester or ether with hydroxyurea and acid. This reaction is particularly useful for preparing a benzo[b]thienyl substituted N-hydroxyurea of formula:

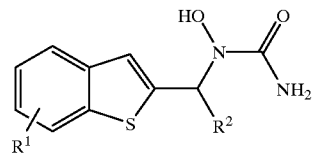

from compound 1:

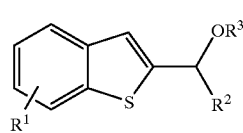

by reacting compound 1 with hydroxyurea and acid. $R^1$ is selected from the group consisting of hydrogen, 1–6 carbon alkyl, 1–6 carbon alkoxy, and halogen; $R^2$ is an 1–4 carbon alkyl; and $R^3$ is selected from the group consisting of hydrogen, acyl, methyl, ethyl and mixtures thereof. Additional steps to isolate the pure bulk product follow.

20 Claims, No Drawings

SYNTHESIS AND ISOLATION OF N-(ARYL OR HETEROARYL)-ALKYL-N-HYDROXYUREA

This application is a conversion of copending provisional U.S. patent application Ser. No. 60/059,663 filed Sep. 25, 1997.

TECHNICAL FIELD

This invention relates to the synthesis and isolation of N-(aryl or heteroaryl)-alkyl-N-hydroxyureas. Examples include N-(benzo[b]thien-2-yl-N-hydroxyureas, in particular, N-(1-benzo[b]thien-2-ylethyl)-N-hydroxyurea.

BACKGROUND OF THE INVENTION

Because leukotrienes have been implicated as important mediators of asthma, allergy, arthritis, psoriasis, and inflammation, agents that inhibit biosynthesis of leukotrienes offer treatment for leukotriene mediated afflictions in man and animals. N-benzo[b]thienyl-N-hydroxyureas, as exemplified by N-(1-benzo[b]thien-2-ylethyl)-N-hydroxyurea (zileuton, U.S. Pat. No. 4,873,259) are potent leukotriene biosynthesis inhibitors. However, N-benzo[b]thienyl-N-hydroxyureas have proven to be a synthetic challenge commercially.

The synthesis of zileuton offers several illustrations of typical methods to prepare benzo[b]thienyl substituted N-hydroxyureas. In one case, one begins by reacting 2-acetylbenzo[b]thiophene with hydroxylamine to form the corresponding oxime. Then the oxime is reduced with an excess of reducing agent, generally borane-pyridine complex, to form 1-benzo[b]thien-2-ylethyl hydroxylamine. Finally, the hydroxylamine is reacted with trimethylsilyl isocyanate or sodium or potassium cyanate to form the corresponding N-hydroxyurea by (see U.S. Pat. No. 4,873,259). Due to the safety considerations and cost involved in using excess reducing agent on a large scale, several alternative preparations of N-(1-benzo[b]thien-2-ylethyl)-N-hydroxyureas have been devised.

One alternative involves reacting (1-benzo[b]thien-2-yl)-1-chloroethane with a nitrogen nucleophile. The nitrogen moiety is then converted to the N-hydroxyurea. However, direct displacement of chloride with hydroxylamine gives a mixture of N- and O-alkylation. Therefore, an O-protected hydroxylamine derivative such as O-benzylhydroxylamine is used as the nitrogen nucleophile (see U.S. Pat. No. 4,873,259). Then the product of the displacement reaction is deprotected to give 1-benzo[b]thien-2-ylethyl hydroxylamine. The hydroxylamine is then converted to the N-hydroxyurea as described above. The displacement has also been accomplished using Z-furfuraldehyde oxime and base to give the nitrone, which is hydrolyzed with acid or reacted with hydroxylamine to give 1-benzo[b]thien-2-ylethyl hydroxylamine (see U.S. Pat. No. 4,873,259). Other O-protected nitrogen nucleophiles such as O-protected hydroxyurea derivatives, for example O-(tetrahydropyran-2-yl)-N-hydroxyurea, have also been used to displace chloride. Removal of the oxygen protecting group provides the N-hydroxyurea (see U.S. Pat. No. 5,292,900).

One process circumvents the conversion of the (1-benzo[b]thien-2-yl)-1-hydroxyethane to the corresponding chloride by using the Mitsunobu coupling. In this process, one first reacts (1-benzo[b]thien-2-yl)-1-hydroxyethane with N,O-bis(phenoxycarbonyl)hydroxylamine. Then, one obtains the corresponding N-hydroxyurea by aminolysis (see A. O. Stewart and D. W. Brooks, *J. Org. Chem.*, 57 (18), 5020 (1992).

The processes described above require either many synthetic steps, and/or protection and deprotection of the hydroxylamine which is expensive and inefficient on a large scale. The pharmaceutical manufacturing industry still seeks a N-substituted-N-hydroxyurea synthesis that can be accomplished in a few steps with a minimum amount of expensive reducing agents or protecting groups.

SUMMARY OF THE INVENTION

The inventors have discovered that reacting a N-(aryl or heteroaryl)-alkyl-(hydroxide, ester, or alkoxide) with hydroxyurea in the presence of acid produces the corresponding N-(aryl or heteroaryl)-alkyl-N-hydroxyurea as shown below.

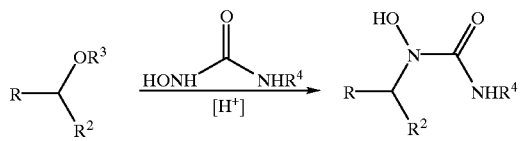

R is selected from the group consisting of substituted or unsubstituted aryl or heteroaryl;

$R^2$ is selected from the group consisting of 1–6 carbon alkyl, aryl, or 3–6 carbon cycloalkyl that is independent or fused with R;

$R^3$ is selected from the group consisting of hydrogen, aralkyl, aryl, 1–6 carbon alkyl, 1–6 carbon alkylcarbonyl, arylcarbonyl, and mixtures thereof; and $R^4$ is selected from the group consisting of hydrogen, aralkyl, aryl, 1–6 carbon alkyl, 1–6 carbon alkylcarbonyl, and arylcarbonyl.

This reaction is particularly useful when (1-benzo[b]thien-2-yl)-1-hydroxyethane or its corresponding ester or alkoxide is reacted with hydroxyurea in acid solution to directly-form N-(1-benzo[b]thien-2-ylethyl)-N-hydroxyurea. Further, Applicants have developed steps after the formation of N-(1-benzo[b]thien-2-ylethyl)-N-hydroxyurea to isolate the product.

In a preferred embodiment, the present invention provides a simple, 1-step process for preparing a benzo[b]thienyl substituted N-hydroxyurea of formula:

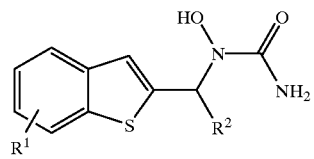

from compound 1:

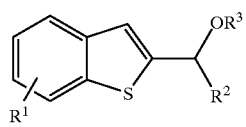

by reacting compound 1 with hydroxyurea and acid. $R^1$ is selected from the group consisting of hydrogen, 1–6 carbon alkyl, 1–6 carbon alkoxy, and halogen; $R^2$ is an 1–4 carbon alkyl; and $R^3$ is selected from the group consisting of hydrogen, acyl, methyl, ethyl and mixtures thereof. Additional steps to isolate the substantially pure bulk product follow.

DETAILED DESCRIPTION OF THE INVENTION

The following definitions are used in this application.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms "alkoxy" or "alkoxyl" refers to an alkyl group, as defined above, attached to the parent molecular moiety through an oxygen atom. Representative alkoxy groups include methoxyl, ethoxyl, propoxyl, butoxyl, and the like.

The terms "aryl" or "heteroaryl" refers to refers to an aromatic moiety or an aromatic moiety that contains a heteroatom respectively.

The functional groups defined above may be connected to known organic functional groups to refer to more complex functionalities. For example, with reference to $R^3$, alkylcarbonyl refers to the ester derivative of the corresponding alcohol such as acetate when alkyl is 1 carbon.

The term "multi" refers to any number greater than 1.

Percentages obtained by HPLC analysis are defined by peak area calculations.

All citations herein are incorporated by reference.

Scheme 1 illustrates the invention by reacting compound 1 with hydroxyurea and acid to form the corresponding N-hydroxyurea. Although the mechanism of this reaction has not been conclusively shown at this time, the reaction is hereinafter referred as the "displacement reaction" without limiting the scope of the invention. The reaction typically utilizes about 5–12 molar equivalents of acid and about 1.5–3.0 molar equivalents of hydroxyurea. Preferred acids include sulfuric acid, trifluoroacetic acid, toluenesulfonic acid, and hydrochloric acid. Hydrochloric acid is particularly preferred. The conversion to desired displacement product is generally greater than about 80% from a ketone starting material that corresponds to compound 1. This is surprising in light of the fact that one could expect alkylation of either oxygen or either nitrogen on the hydroxyurea to produce a mixture of products. Based on statistics alone, one would expect about a 25% conversion to the desired displacement product.

Typical solvents for the reaction, which can be used singly or in combination, include water, acetic acid, benzene, toluene, xylene, esters such as ethyl acetate and isopropyl acetate, acetonitrile, alcohols, for example methanol, ethanol, or propanol, ethers such as ethyl ether, and methyl t-butyl ether, and tetrahydrofuran. The reaction mixture may be heated, preferably to about 40–60° C. In a preferred embodiment, compound 1 is reacted with about 5–6 equivalents of acid and about 1.0–1.8 equivalents of hydroxyurea at a temperature of about 40° C. Hydroxyurea may be prepared in advance and dissolved in the solvent of choice for the displacement reaction, or may be prepared and used as an aqueous solution without further purification. A representative procedure for the preparation and isolation of hydroxyurea is described in Org. Syn., 40, 60 (1960). In a particularly preferred embodiment, hydroxyurea is prepared in aqueous solution by treatment of methyl carbamate with aqueous hydroxylamine and aqueous sodium hydroxide, and the solution is used as-is in the displacement reaction.

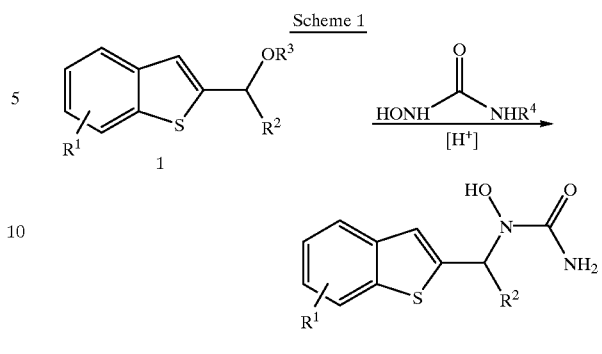

Scheme 1

Compound 1 is prepared by reducing the corresponding ketone via any of a number of methods known in the art for reducing ketones as shown in Scheme 2. Representative reducing agents include lithium aluminum hydride, sodium borohydride, sodium cyanoborohydride, borane-THF, and dialkyl aluminum hydrides such as diisopropylaluminum hydride. Reduction solvents include esters such as ethyl acetate and isopropyl acetate, acetonitrile, alcohols, for example methanol, ethanol, or propanol, ethers such as ethyl ether, and methyl t-butyl ether, tetrahydrofuran, and aqueous acetonitrile. In a particularly preferred embodiment, the reaction mixture from the reduction reaction is added directly to an aqueous solution of hydroxyurea, followed by acid. Although, the product of the reduction is expected to by the hydroxyl compound, the corresponding ester has been found in the reduction ($R^3$ selected H and 1–6 carbon alkylcarbonyl such as acyl). However, both the hydroxide and the ester, as well as any ether products, can be used without further purification in the displacement reaction.

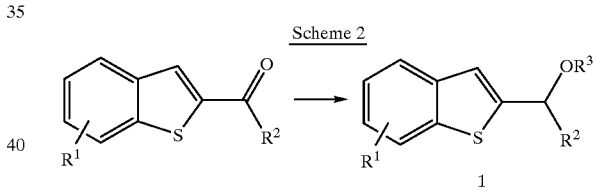

Scheme 2

Purifying desired displacement product from the displacement reaction mixture is accomplished by a series of solvent additions, pH adjustments, and phase separations, during which impurities are removed by means of intimate phase contacting and subsequent separation of waste phases. First, an organic solvent such as tetrahydrofuran (THF), methyl-tert-butyl ether (MTBE), toluene, ethyl acetate (EtOAc), or a combination thereof is added to the displacement reaction mixture. THF is particularly preferred. Water is optionally added. Addition of base, preferably sodium hydroxide, brings the mixture to near-neutral pH, typically between about pH 4–7. Then the mixture is heated and mixed, preferably to about 40–60° C., then allowed to separate to create a multi-phase system. The aqueous layer is discarded while the organic layer is reserved for further processing. A variation on the above steps has been employed in which the pH is adjusted to an intermediate pH, typically between about pH 0–2, at which point the mixture is heated and the phases separated. Additional water and/or tetrahydrofuran may be added, at which point the mixture is adjusted to about pH 4–7, heated, and separated as described above.

A dilute solution of base of sufficient concentration and volume to dissolve the product, preferably about 5–15% aqueous sodium hydroxide, is added to the organic layer.

Then an organic solvent such as MTBE, toluene, EtOAc or a combination thereof is added. Toluene is particularly preferred. The resulting multi-phase system is mixed under ambient conditions for an amount of time sufficient for thorough phase contact (at least about 5 minutes). Then, the organic phase is discarded.

An organic solvent such as THF, MTBE, toluene, EtOAc or a combination thereof is added to the aqueous phase. EtOAc is particularly preferred. An acid, preferably hydrochloric or sulfuric acid, is added to precipitate the product out of solution. Hydrochloric acid is particularly preferred. The result is a multi-phase system, comprising a product slurry phase and an aqueous phase. The aqueous waste phase is discarded. A variation has been employed in which an organic solvent is added to the mixture prior to separation to increase the immiscibility between phases prior to separation. Preferred solvents included MTBE, toluene, EtOAc, heptane, and combinations thereof. Toluene is particularly preferred. Additional organic solvents as defined above may then be added to thin the slurry so that it may be more efficiently washed with water to remove water-soluble impurities. Toluene is particularly preferred. The water washes are carried out by adding a volume of water to the product slurry, mixing, and then discarding the water wash phase. Multiple water washes may be employed. The product is then isolated, preferably by filtration or centrifugation, washed with an organic solvent, preferably, MTBE, toluene or heptane, most preferably toluene, dried and milled into powder from lumps of product.

The overall yield based on the ketone starting material is at least about 70–80% of a high analytically pure product. This is a surprisingly high yield considering that the product of the reduction of the ketone and the product of the formation of the hydroxyurea starting material can be used without further isolation in the displacement reaction. As noted above, it is also surprising considering that the hydroxyurea starting material has four sites of reaction that could have resulted in a statistical distribution of O and N alkylated products.

The foregoing may be better understood by the following example, which is presented for purposes of illustration and is not intended to limit the scope of the invention.

Preparation of N-(1-benzo[b]thien-2-ylethyl)-N-hydroxyurea (zileuton)

Step 1: Hydroxyurea

Methyl carbamate (320 kg, 4.3 kmol) and 50% aqueous hydroxylamine (310 kg, 4.7 kmol) were combined as mixture 1. This combination produced an endotherm which brought mixture 1 to about 4–5° C. Fifty percent aqueous sodium hydroxide (338 kg, 4.2 kmol) was added to mixture 1 to make mixture 2. The rate of addition was sufficiently slow to avoid exothermic overheating. The resulting exotherm was also controlled by, for example, a cooling jacket to maintain a temperature of between about 5–30° C. Then the temperature of mixture 2 was adjusted to about 25° C. and stirred for about four hours. HPLC analysis of mixture 2 indicated about 276 mg hydroxyurea per gram of mixture 2.

Step 2: (1-benzo[b]thien-2-yl)-1-hydroxyethane

Sodium borohydride (32.3 kg, 0.9 kmol), 2-acetylbenzo[b]thiophene (500 kg, 2.8 kmol), and 458 kg ethyl acetate were combined as mixture 3 in a separate reactor from mixture 2. Methanol (80 kg) was added to mixture 3 to produce mixture 4 and an exotherm which brought mixture 4 to reflux. Once again the rate of addition must be sufficiently slow to prevent the exotherm from running away. Preferably, the methanol is added in portions. Mixture 4 was maintained at reflux for about 45 minutes, and then cooled to about 25° C. HPLC analysis of mixture 4 indicated about 79% of the alcohol product and about 20% of the acetate product for an essentially quantitative reduction yield.

Step 3: N-(1-benzo[b]thien-2-ylethyl)-N-hydroxyurea (zileuton)

Mixtures 2 and 4 were combined as-is and cooled to about 5° C. to produce mixture 5. Muriatic acid (31.5% aqueous HCl, 6 equivalents) was added to form mixture 6. The resulting exotherm was controlled by a sufficiently slow rate of addition and/or by external cooling, so that the temperature of the reaction mixture during the addition was maintained between about 5–30° C. After adding the acid, the temperature of mixture 6 was adjusted to about 40° C. and stirred for about six hours. HPLC analysis of mixture 6 indicated about 87% desired product.

Step 4: Purification

Tetrahydrofuran (873 kg) and water (404 kg) was added to mixture 6. The mixture was cooled to about 5° C. While maintaining the mixture temperature between about 5–30° C., 50% aqueous sodium hydroxide was added until the pH was adjusted to about 0.09 from below zero. The mixture was then heated to about 48° C. until product is dissolved and a multi-phase system comprising an organic layer and an aqueous layer was produced. The aqueous layer was separated and discarded.

Water (about 402 kg), tetrahydrofuran (about 237 kg) and sufficient amounts of about 50% aqueous sodium hydroxide was added to the mixture to obtain a pH of about 4.5. Once again the rate of addition is limited by the need to control the exotherm from the addition. The mixture was heated to about 48° C. for a sufficient time to obtain another multi-phase system. The aqueous layer was separated and discarded.

While maintaining the temperature of the mixture between about 5–30° C., 2508 kg of an about 10% aqueous sodium hydroxide solution was added to the organic layer at a sufficiently slow rate to control the exotherm. At this point, the mixture was essentially a single-phase aqueous system comprising the essentially dissolved product. Toluene (429 kg) was added to this mixture to produce a multi-phase system. The aqueous layer was separated to a different reactor and the organic layer was discarded. Ethyl acetate (926 kg) and muriatic acid (31.5% HCl) was added to the aqueous layer to obtain a pH of about 2.5, thereby precipitating the product. Once again the rate of addition was dictated by the desire to control the exotherm from the addition. The temperature of the mixture during the acid addition was maintained between about 5–30° C. Toluene (538 kg) was added to the mixture to produce an organic slurry and an aqueous layer. The aqueous layer was separated and discarded.

Toluene (637 kg) and about 2000 kg water was added to the organic slurry to again produce a slurry layer and an aqueous layer. The aqueous layer was separated and discarded. Two additional water washes (about 2000 kg each) were carried out as above. The product slurry was filtered to isolate the product, washed with toluene (1875 kg) and dried at a jacket temperature of between about 20–80° C. under vacuum (about 5–100 mm Hg absolute pressure). The yield of the displacement product was about 71.2% (from the ketone starting material). This product was 99.94% pure by HPLC.

Additional Displacement Reactions

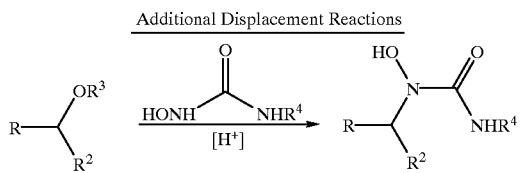

Additional examples of the hydroxyurea displacement reaction are shown in the table below.

| Starting Material | Temp. (° C.) | Time (Hrs) | HPLC Yield |
|---|---|---|---|
| benzothiophene-2-yl ethanol | 50 | 4 | 91 |
| benzothiophene-3-yl ethanol | 50 | 6 | 30 |
| thiophen-2-yl ethanol | 50 | 6 | 59 |
| benzofuran-2-yl ethanol | 50 | 2 | 89 |
| furan-2-yl ethanol | 50 | 2 | 66 |
| furan-2-yl ethanol | 25 | ¾ | 52 |
| pyridin-2-yl ethanol | 50 | 6 | 0 |
| 1-phenylethanol | 50 | 6 | 4.5 |
| 1,2,3,4-tetrahydronaphthalen-1-ol | 50 | 6 | 90 |
| diphenylmethanol | 50 | 6 | 85 |
| 1-(2-methoxyphenyl)ethanol | 50 | 6 | 50 |
| 1-(4-methoxyphenyl)ethanol | 50 | 6 | 58 |

We claim:

1. A process for preparing an aryl substituted N-hydroxyurea having the structure:

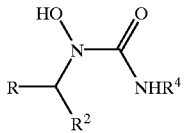

comprising mixing a compound of formula:

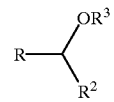

with hydroxyurea and acid;

wherein R is selected from the group consisting of substituted or unsubstituted aryl and heteroaryl;

$R^2$ is selected from the group consisting of 1–6 carbon alkyl, aryl and 3–6 carbon cycloalkyl that is independent or fused with R;

$R^3$ is selected from the group consisting of hydrogen, aralkyl, aryl, 1–6 carbon alkyl, 1–6 carbon alkylcarbonyl, and arylcarbonyl; and $R^4$ is selected from the group consisting of hydrogen, aralkyl, aryl, 1–6 carbon alkyl, 1–6 carbon alkylcarbonyl, and arylcarbonyl.

2. The process of claim 1 wherein the compound of the formula:

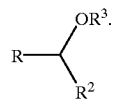

is selected from the group consisting of:

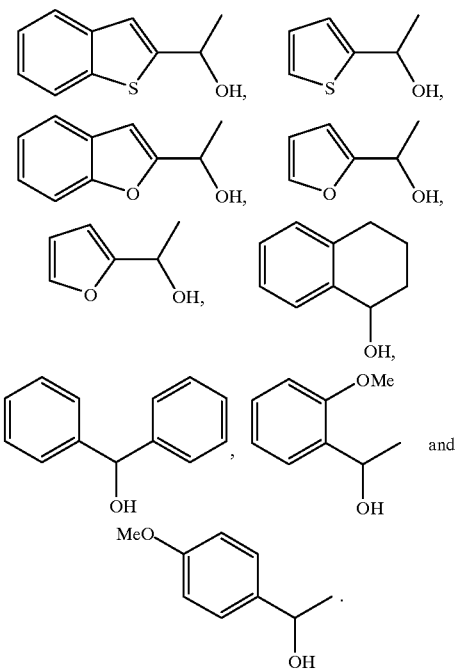

3. A process for preparing a benzo[b]thienyl substituted N-hydroxyurea of formula:

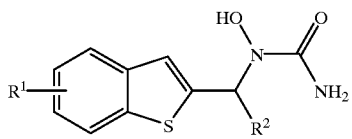

comprising mixing a compound of formula 1:

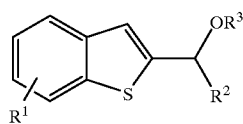

with hydroxyurea and acid;
wherein $R^1$ is selected from the group consisting of hydrogen, 1–6 carbon alkyl, 1–6 carbon alkoxy, and halogen;
$R^2$ is a 1–4 carbon alkyl; and
$R^3$ is selected from the group consisting of hydrogen, aralkyl, aryl, 1–6 carbon alkyl, 1–6 carbon alkylcarbonyl and arylcarbonyl; and, then recovering a reaction mixture of the benzo[b]thienyl substituted N-hydroxyurea.

4. The process of claim 3 wherein the acid is selected from the group consisting of HCl, $H_2SO_4$, trifluoroacetic acid, and toluenesulfonic acid.

5. The process of claim 3 wherein the acid is HCl.

6. The process of claim 3 wherein $R^1$ is H, $R^2$ is methyl, $R^3$ is selected from the group consisting of H, acyl, methyl, and ethyl, and the acid is HCl.

7. The process of claim 3 wherein the compound of formula 1 is prepared by reducing the corresponding ketone with a reducing agent sufficient to convert substantially all of the ketone to a reduced product, and, without further purification, the reduced product is mixed with the hydroxyurea followed by the acid.

8. The process of claim 7 wherein the acid is selected from the group consisting of HCl, $H_2SO_4$, trifluoroacetic acid, and toluenesulfonic acid.

9. The process of claim 7 wherein said acid is HCl.

10. The process of claim 7 wherein $R^1$ is H and $R^2$ is methyl.

11. The process of claim 7 wherein the hydroxyurea is prepared by reacting methyl carbamate with aqueous hydroxylamine and aqueous sodium hydroxide.

12. The process of claim 11 wherein the acid is HCl.

13. The process of claim 3 further comprising purifying the benzo[b]thienyl substituted-N-hydroxyurea by the steps comprising,
(a) adding an first organic solvent to the reaction mixture;
(b) adding base to the mixture of step (a) to bring the pH to between about 4–7; and
(c) separating the aqueous phase from the organic phase.

14. The process of claim 3 further comprising purifying the benzo[b]thienyl substituted-N-hydroxyurea by the steps comprising,
(a) adding a first organic solvent to the reaction mixture;
(b) adding base to the mixture of step (a) to bring the pH to between about 4–7;
(c) heating the mixture of step (b) to dissolve the desired product, and discarding the aqueous phase from the organic phase;
(d) adding sufficient dilute aqueous NaOH to the organic phase of step (c) to dissolve the benzo[b]thienyl-substituted-N-hydroxyurea, admixing a second organic solvent, and discarding the organic phase from the aqueous phase;
(e) adding a third organic solvent to the aqueous phase of step (d), followed by sufficient amounts of an acid to precipitate the product to form at least an organic slurry and an aqueous phase, and discarding the aqueous phase;
(f) washing the organic slurry of step (e) with water, filtering the precipitates, washing the precipitates with a fourth organic solvent, and drying the precipitates.

15. The process of claim 3 further comprising purifying the benzo[b]thienyl-substituted-N-hydroxyurea by the steps comprising,
(a) adding an first organic solvent to the reaction mixture;
(b) adding base to the mixture of step (a) to bring the pH to between about 0–2, heating the mixture, and adding water and/or first organic solvent;
(c) adding base to the mixture of step (b) to bring the pH to between about 4–7; and
(d) separating the aqueous phase from the organic phase.

16. The process of claim 3 further comprising purifying the benzo[b]thienyl-substituted-N-hydroxyurea by the steps comprising,
(a) adding an first organic solvent to the reaction mixture;
(b) adding base to the mixture of step (a) to bring the pH to between about 0–2, heating the mixture, and adding water and/or first organic solvent;
(c) adding base to the mixture of step (b) to bring the pH to between about 4–7;
(d) heating the mixture of step (c) to create at least one aqueous phase and one organic phase, and discarding the aqueous phase from the organic phase;

(e) adding sufficient dilute aqueous NaOH to the organic phase of step (d) to dissolve the benzo[b]thienyl-substituted-N-hydroxyurea, admixing a second organic solvent, and discarding the organic phase from the aqueous phase;

(f) adding a third organic solvent to the aqueous phase of step (e), followed by sufficient amounts of an acid to precipitate the product to form at least an organic slurry and an aqueous phase, optionally admixing a fourth organic solvent and discarding the aqueous phase;

(g) washing the organic slurry of step (f) with water, filtering the precipitates, washing the precipitates with a fifth organic solvent, and drying the precipitates.

17. The process of claim 16 wherein the first organic solvent is selected from the group consisting of tetrahydrofuran, methyl-tert-butyl ether, toluene, ethyl acetate or a combination thereof, the second organic solvent is selected from the group consisting of toluene, ethyl acetate, methyl-tert-butyl ether or a combination thereof, the third organic solvent is selected from the group consisting of tetrahydrofuran, methyl-tert-butyl ether, toluene, ethyl acetate or a combination thereof, and the acid of step (f) is selected from the group consisting of HCl and $H_2SO_4$.

18. The process of claim 16 wherein the first organic solvent is tetrahydrofuran, the base is sodium hydroxide, the second organic solvent is toluene, the third organic solvent is ethyl acetate, the acid of step (f) is HCl, the fourth organic solvent is toluene, and the fifth organic solvent is toluene.

19. The process of claim 18 wherein $R^1$ is H and $R^2$ is methyl.

20. The process of claim 3 wherein the compound of formula 1 is added to an aqueous solution of hydroxyurea followed by the acid, and a reaction mixture of the benzo[b]thienyl substituted N-hydroxyurea is recovered.

* * * * *

UNITED STATES PATENT AND TRADEMARK OFFICE
CERTIFICATE OF CORRECTION

PATENT NO.    : 6,080,874
DATED         : June 27, 2000
INVENTOR(S)   : John E. Hengeveld et al.

Page 1 of 1

It is certified that error appears in the above-identified patent and that said Letters Patent is hereby corrected as shown below:

Replace: 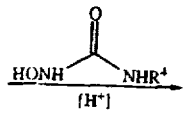

With:

Scheme I

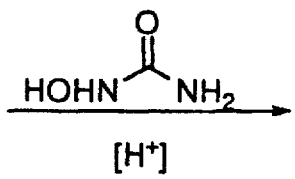

Signed and Sealed this

Twelfth Day of March, 2002

Attest:

JAMES E. ROGAN
Attesting Officer   Director of the United States Patent and Trademark Office